United States Patent
Fujisaki et al.

(10) Patent No.: US 9,249,056 B2
(45) Date of Patent: Feb. 2, 2016

(54) COLORED TRANSLUCENT ZIRCONIA SINTERED BODY AND ITS USE

(75) Inventors: Hiroyuki Fujisaki, Yamaguchi (JP); Kiyotaka Kawamura, Yamaguchi (JP); Kohei Imai, Kanagawa (JP)

(73) Assignee: TOSOH CORPORATION, Shunan-shi (JP)

( * ) Notice: Subject to any disclaimer, the term of this patent is extended or adjusted under 35 U.S.C. 154(b) by 0 days.

(21) Appl. No.: 14/235,716

(22) PCT Filed: Jul. 27, 2012

(86) PCT No.: PCT/JP2012/069232
§ 371 (c)(1),
(2), (4) Date: Mar. 21, 2014

(87) PCT Pub. No.: WO2013/018728
PCT Pub. Date: Feb. 7, 2013

(65) Prior Publication Data
US 2014/0227654 A1    Aug. 14, 2014

(30) Foreign Application Priority Data

Jul. 29, 2011 (JP) ................... 2011-166358
Jul. 29, 2011 (JP) ................... 2011-166359

(51) Int. Cl.
*C04B 35/486*    (2006.01)
*C04B 35/48*    (2006.01)
(Continued)

(52) U.S. Cl.
CPC . *C04B 35/48* (2013.01); *A61C 7/14* (2013.01); *A61C 13/082* (2013.01); *A61L 27/047* (2013.01);
(Continued)

(58) Field of Classification Search
CPC ...... C04B 35/48; C04B 35/486; A61L 27/10; A61L 27/105; A61C 13/083
See application file for complete search history.

(56) References Cited

U.S. PATENT DOCUMENTS 5,263,858 A * 11/1993 Yoshida et al. .......... 433/8
7,553,789 B2   6/2009 Fujisaki
(Continued)

FOREIGN PATENT DOCUMENTS

CN    101172838 A    5/2008
EP    1859757 A2    11/2007
(Continued)

OTHER PUBLICATIONS

Machine translation of 2008-50246, Mar. 2008.*
(Continued)

*Primary Examiner* — Karl Group
(74) *Attorney, Agent, or Firm* — Westerman, Hattori, Daniels & Adrian, LLP

(57) ABSTRACT

A zirconia sintered body having not only high strength but also excellent aesthetic properties. A colored translucent zirconia sintered body, characterized by containing an iron compound and from 2 to 4 mol % of yttria, showing a lightness L* of from 51 to 80 in L*a*b* color system, and having a relative density of at least 99.80%. The colored zirconia sintered body preferably has a total light transmittance of at least 20% as measured at a sample thickness of 1 mm and with a D65 light source. The colored translucent zirconia sintered body has aesthetic properties equivalent to those of natural teeth and is particularly suitable for a zirconia sintered body to be used for dental applications, and further, suitable for a mill blank such as an artificial tooth material or the like, and an orthodontic bracket.

13 Claims, 4 Drawing Sheets

(51) Int. Cl.
  *C04B 35/626* (2006.01)
  *C04B 35/645* (2006.01)
  *A61C 7/14* (2006.01)
  *A61C 13/08* (2006.01)
  *A61L 27/04* (2006.01)

(52) U.S. Cl.
  CPC .......... *C04B 35/486* (2013.01); *C04B 35/6261* (2013.01); *C04B 35/6263* (2013.01); *C04B 35/6455* (2013.01); *C04B 2235/3217* (2013.01); *C04B 2235/3225* (2013.01); *C04B 2235/3272* (2013.01); *C04B 2235/44* (2013.01); *C04B 2235/5409* (2013.01); *C04B 2235/5436* (2013.01); *C04B 2235/5445* (2013.01); *C04B 2235/604* (2013.01); *C04B 2235/6562* (2013.01); *C04B 2235/72* (2013.01); *C04B 2235/765* (2013.01); *C04B 2235/77* (2013.01); *C04B 2235/785* (2013.01); *C04B 2235/81* (2013.01); *C04B 2235/96* (2013.01); *C04B 2235/9615* (2013.01); *C04B 2235/9653* (2013.01); *C04B 2235/9661* (2013.01); *C04B 2235/9669* (2013.01)

(56) References Cited

U.S. PATENT DOCUMENTS

| | | |
|---|---|---|
| 8,304,356 B2 | 11/2012 | Fukatani et al. |
| 2009/0246735 A1 | 10/2009 | Rogowski et al. |
| 2011/0027742 A1 | 2/2011 | Fujisaka et al. |
| 2013/0217562 A1 | 8/2013 | Yamauchi et al. |

FOREIGN PATENT DOCUMENTS

| | | |
|---|---|---|
| JP | 62-59571 A | 3/1987 |
| JP | 2006-298711 A | 11/2006 |
| JP | 2008-50246 A | 3/2008 |
| JP | 2008-50247 A | 3/2008 |
| JP | 2008050246 * | 3/2008 |
| JP | 2009-207743 A | 9/2009 |
| JP | 2010-501465 A | 1/2010 |
| JP | 2011-20876 A | 2/2011 |
| JP | 2012-116745 A | 6/2012 |
| WO | 2009/125793 A1 | 10/2009 |

OTHER PUBLICATIONS

International Search Report dated Oct. 16, 2012 issued in corresponding application No. PCT/JP2012/069232.
Extended European Search Report dated Jan. 9, 2015, issued in corresponding European Patent Application No. 12820547.3 (6 pages).
Notification of Transmittal of Translation of the International Preliminary Report on Patentabililty (Form PCT/IB/338) of International Application No. PCT/JP2012/069232 mailed Feb. 13, 2014 with Forms PCT/IB/373 and PCT/ISA/237 (10 pages).
With English translation of Nagayama, H. et al., "Development of colored zirconia sintered body", TOSOH Research & Technology Review vol. 53, 2009, pp53-56 (15 pages).

* cited by examiner

COLORED TRANSLUCENT ZIRCONIA SINTERED BODY AND ITS USE

TECHNICAL FIELD

The present invention relates to a zirconia sintered body having not only high strength but also aesthetic properties quite similar to those of natural teeth.

BACKGROUND ART

Zirconia sintered body has high strength, whereby it has been used as dental materials. When the zirconia sintered body is used as a dental material, it is required to have not only high strength but also aesthetic properties similar to those of natural teeth.

Heretofore, to obtain a zirconia sintered body aesthetically comparable to natural teeth, a dental material prepared by laminating, on the surface of zirconia sintered body, other materials so as to adjust its color tone has been reported (Patent Document 1). However, since such a dental material is a composite material made of a glass material having a strength different from that of zirconia, its strength has not been sufficient for a dental material.

Therefore, a zirconia sintered body for dental materials which has increased aesthetic properties, without laminating other materials, while maintaining its strength has been studied.

For example, it has been reported that a zirconia sintered body having a translucency equivalent to that of natural teeth can be prepared by imparting translucency thereto. Patent Documents 2 and 3 disclose a zirconia sintered body, which will be used as a dental material as it is, having high strength and high translucency. However, although such a zirconia sintered body was found to show a translucency equivalent to that of natural teeth, its bright white color tone derived from zirconia was found to be different from the color tone of natural teeth.

Further, a colored zirconia sintered body for dental materials which contains oxides as a coloring agent has been reported (Patent Document 4). However, in such a colored zirconia sintered body, visible lights are absorbed by a coloring component contained therein. In addition, the translucency of such a sintered body is low since the coloring component inhibits the sintering process. Accordingly, such a colored zirconia sintered body was found to have a translucency and color tone different from those of natural teeth, and also have low strength.

PRIOR ART DOCUMENTS

Patent Documents

Patent Document 1: JP-A-2009-207743
Patent Document 2: JP-A-2008-50247
Patent Document 3: WO2009/125793
Patent Document 4: JP-A-2010-501465

DISCLOSURE OF INVENTION

Technical Problem

Heretofore, a zirconia sintered body having aesthetic properties equivalent to those of natural teeth, particularly a color tone and translucency equivalent to those of natural teeth, and having high strength has not been obtained yet.

The object of the present invention is to provide a zirconia sintered body having not only high strength but also excellent aesthetic properties, thereby to solve the above-described problems.

Solution to Problem

Under these circumstances, the present inventors have conducted extensive studies on the relation between the color tone and the aesthetic properties of a zirconia sintered body. As a result, the present inventors have found that a zirconia sintered body having controlled compositions, physical properties and types of a coloring agent has aesthetic properties and strength suitable for dental materials, and thus have accomplished the present invention.

The present invention has the following features.

(1) A colored translucent zirconia sintered body, characterized by containing an iron compound and from 2 to 4 mol % of yttria, showing a lightness $L^*$ of from 51 to 80 in $L^*a^*b^*$ color system, and having a relative density of at least 99.80%.
(2) The colored translucent zirconia sintered body according to the above (1), wherein the lightness $L^*$ is from 51 to 70 in $L^*a^*b^*$ color system.
(3) The colored translucent zirconia sintered body according to the above (1), wherein the lightness $L^*$ is more than 70 and at most 80 in $L^*a^*b^*$ color system.
(4) The colored translucent zirconia sintered body according to any one of the above (1) to (3), which has a total light transmittance of at least 20% as measured at a sample thickness of 1 mm and with a D65 light source.
(5) The colored translucent zirconia sintered body according to any one of the above (1) to (4), wherein the content of the iron compound is less than 2,000 ppm as calculated as $Fe_2O_3$.
(6) The colored translucent zirconia sintered body according to any one of the above (1) to (5), wherein the content of the iron compound is at least 500 ppm as calculated as $Fe_2O_3$.
(7) The colored translucent zirconia sintered body according to any one of the above (1) to (5), wherein the content of the iron compound is less than 500 ppm as calculated as $Fe_2O_3$.
(8) The colored translucent zirconia sintered body according to any one of the above (1) to (7), which further contains alumina.
(9) The colored translucent zirconia sintered body according to the above (8), wherein the content of alumina is less than 0.25 wt %.
(10) The colored translucent zirconia sintered body according to the above (9), which has a monoclinic phase transformation depth of at most 10 μm after immersion in a hot water of 140° C. for 24 hours.
(11) The colored translucent zirconia sintered body according to the above (10), which has a monoclinic phase transformation depth of at most 10 μm after immersion in a hot water of 140° C. for 72 hours.
(12) A dental material obtained by using the colored translucent zirconia sintered body as defined in any one of the above (1) to (11).
(13) The dental material according to the above (12), which is an orthodontic bracket.
(14) The dental material according to the above (12), which is an artificial tooth or an artificial tooth mill blank, or both of them.

Advantageous Effects of Invention

The colored translucent zirconia sintered body of the present invention has a color tone and translucency equivalent to those of natural teeth, and further has high strength. Therefore, the colored translucent zirconia sintered body of the present invention is a sintered body suitable for dental materials, and is a sintered body particularly suitable for a mill blank such as an artificial tooth material and an orthodontic bracket.

DESCRIPTION OF EMBODIMENTS

Figure 1:
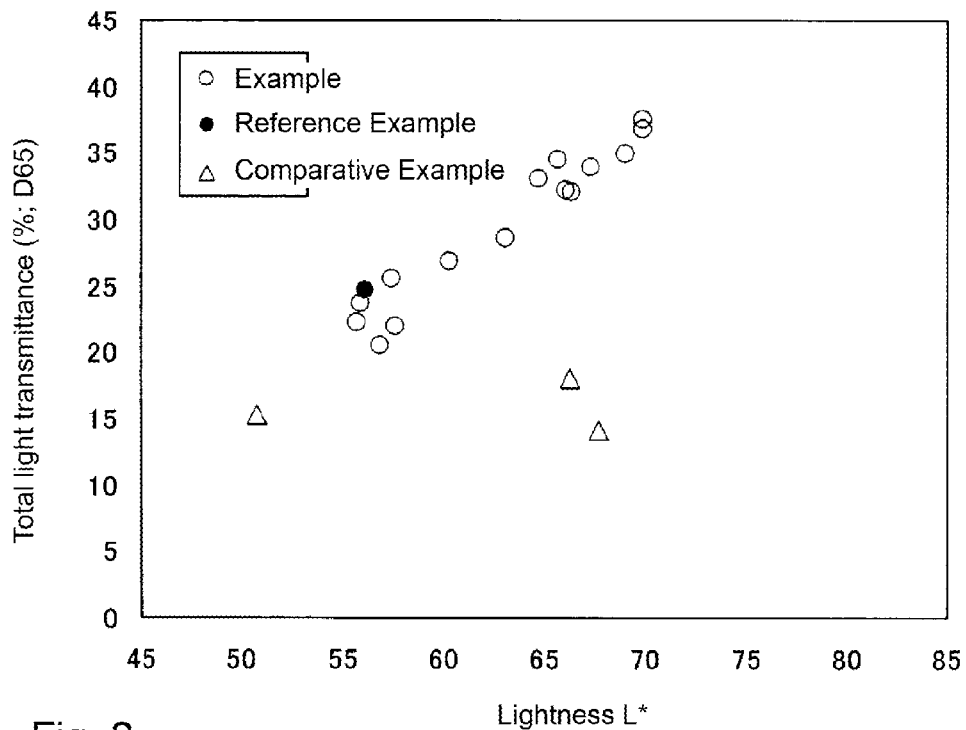
FIG. 1 illustrates the relation between the lightness L* and the total light transmittance (a total light transmittance as measured with a D65 light source) in Examples 1 to 15 and Comparative Examples 1 to 3.
Figure 2:
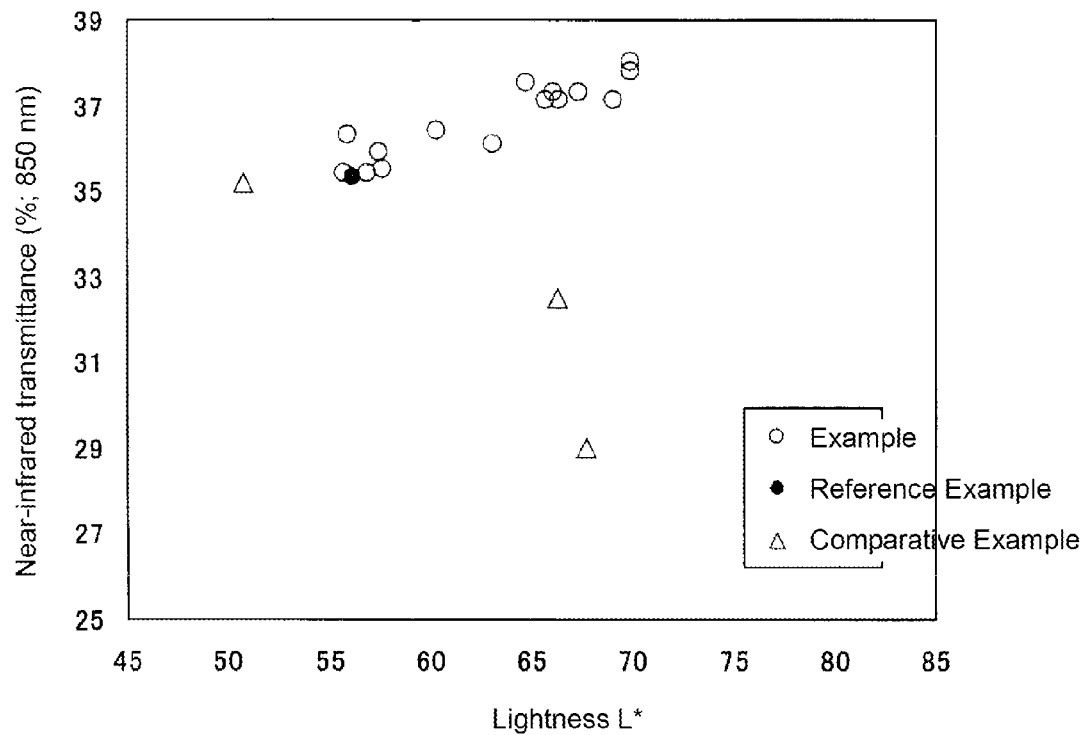
FIG. 2 illustrates the relation between the lightness L* and the near-infrared transmittance (a total light transmittance as measured at a wavelength of 850 nm) in Examples 1 to 15 and Comparative Examples 1 to 3.
Figure 3:
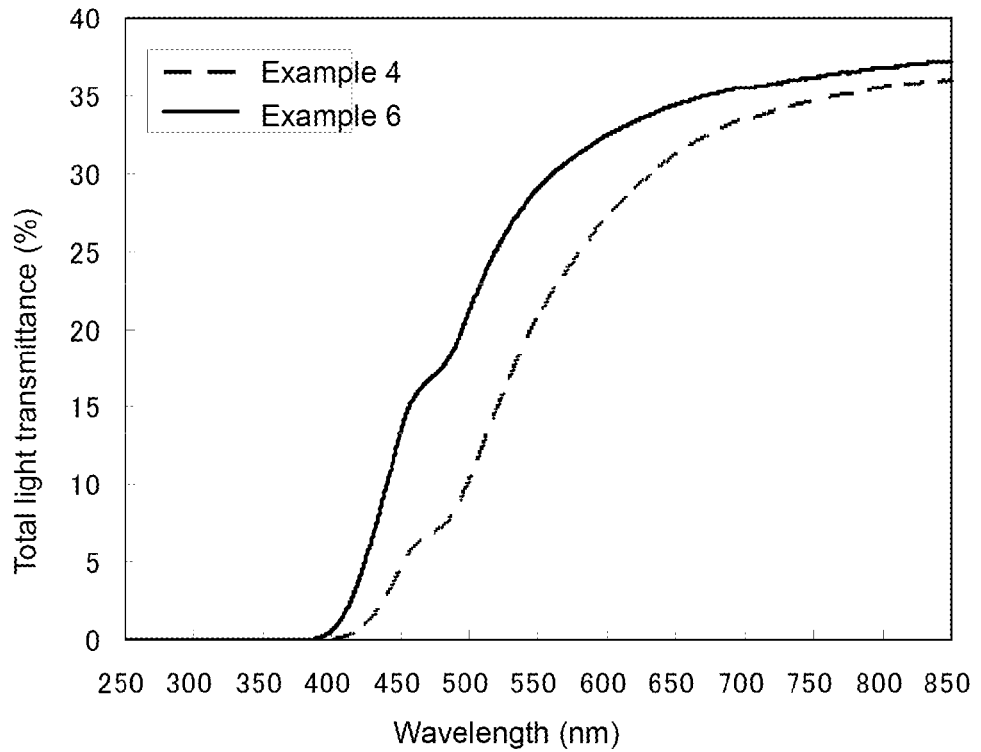
FIG. 3 illustrates the measurement wavelength dependency of the total light transmittance in each of Example 4 and Example 6.
Figure 4:
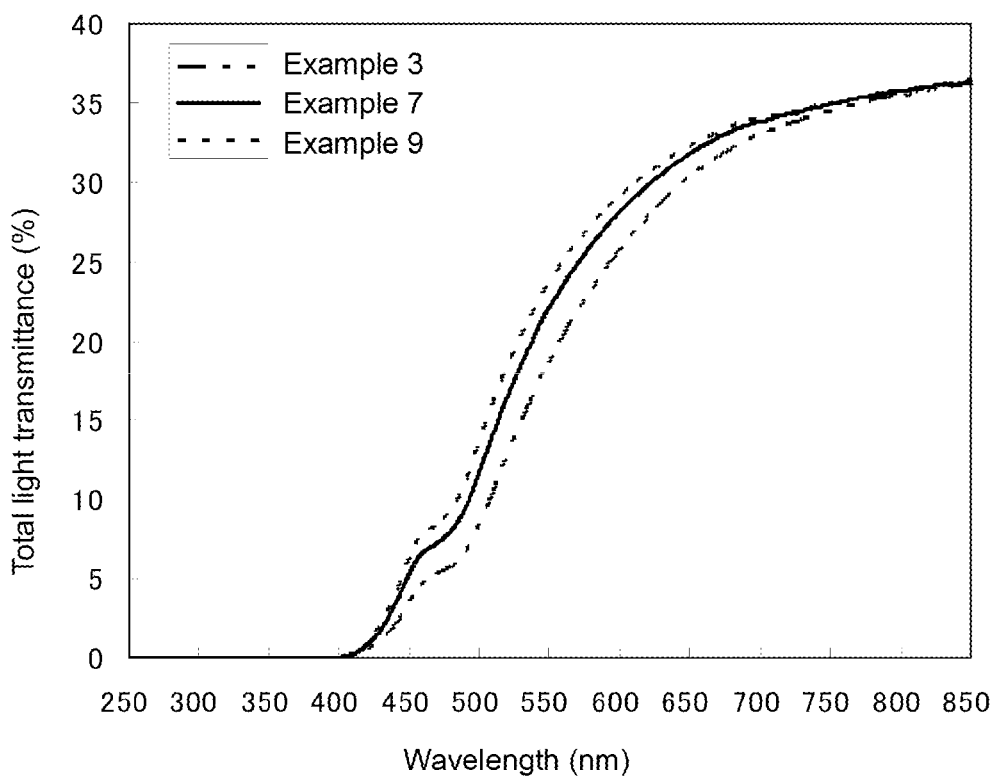
FIG. 4 illustrates the measurement wavelength dependency of the total light transmittance in each of Example 3, Example 7 and Example 9.
Figure 5:
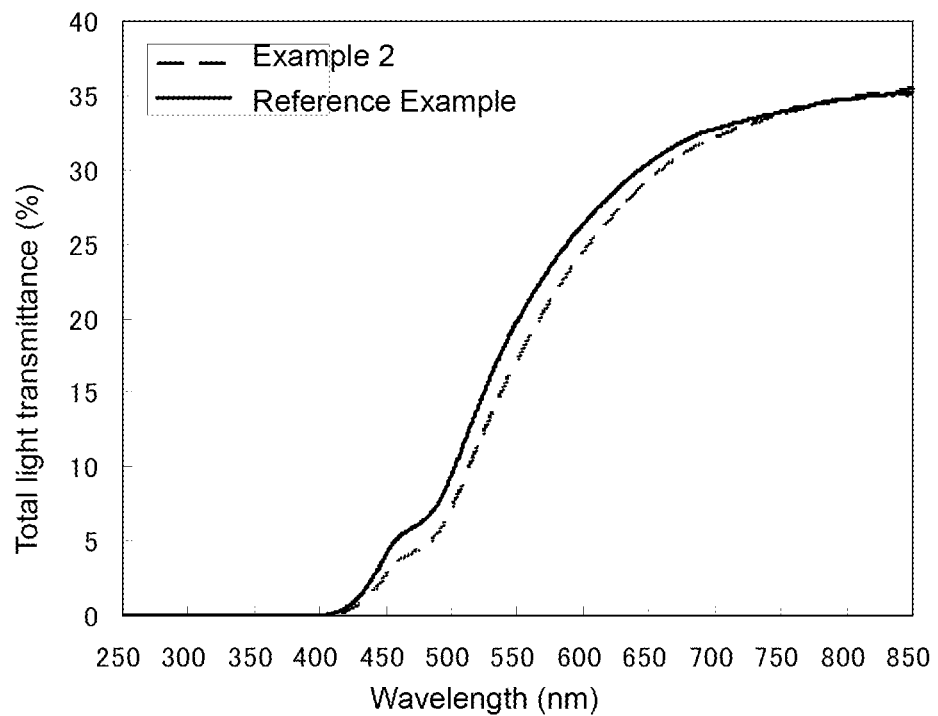
FIG. 5 illustrates the measurement wavelength dependency of the total light transmittance in each of Example 2 and Reference Example for the comparison.
Figure 6:
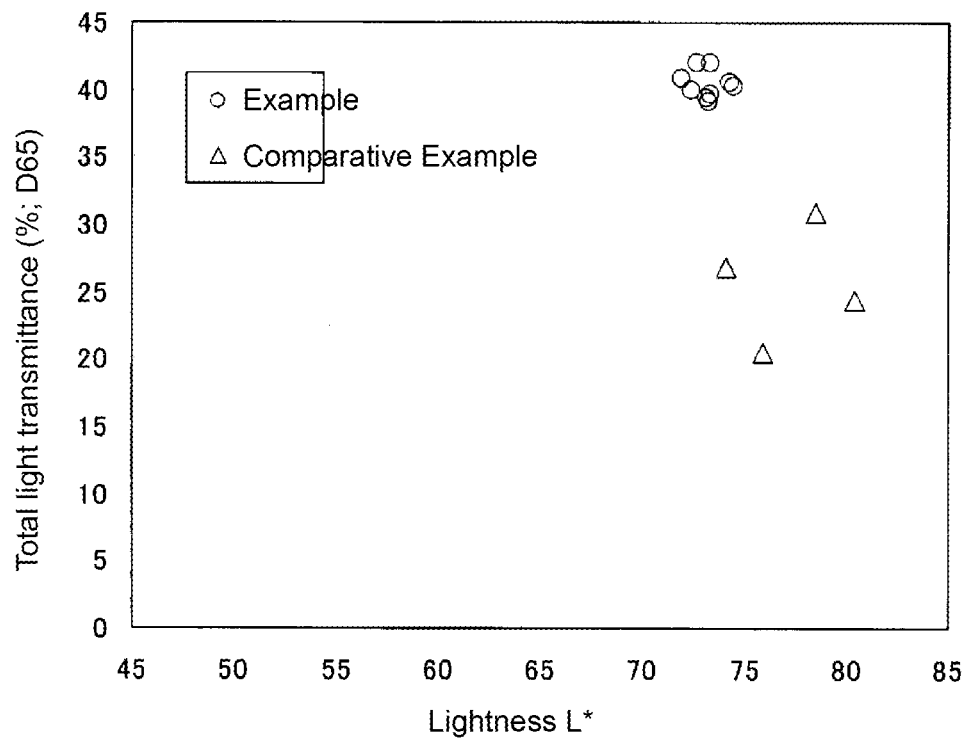
FIG. 6 illustrates the lightness L* and the total light transmittance (a total light transmittance as measured with a D65 light source) in each of Examples 16 to 25 and Comparative Examples 4 to 7.
Figure 7:
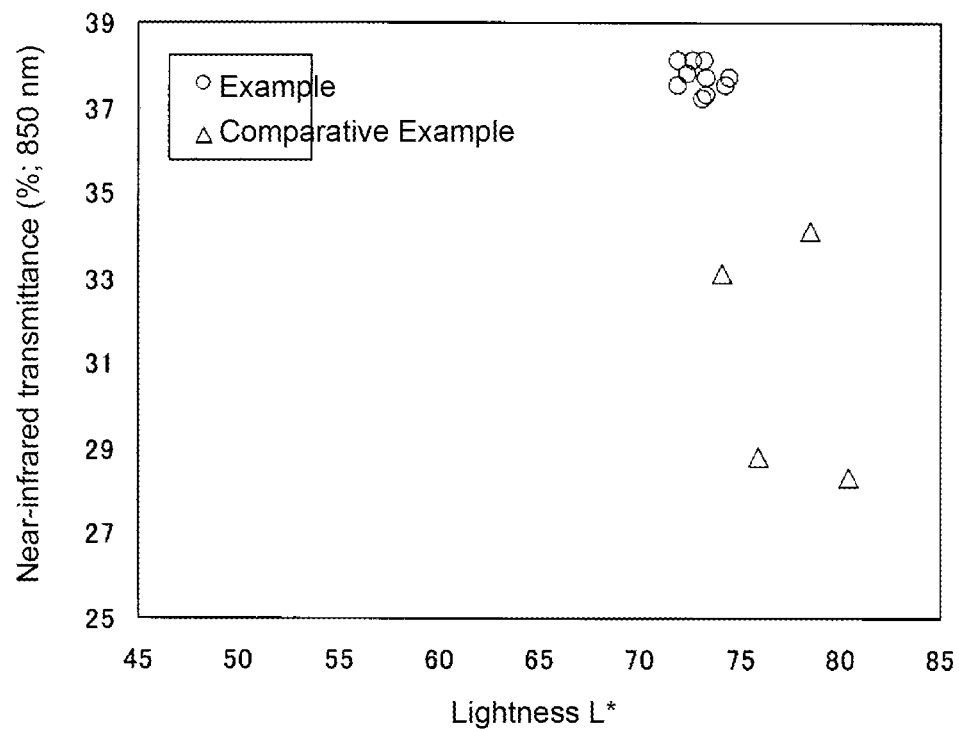
FIG. 7 illustrates the lightness L* and the near-infrared transmittance (a total light transmittance as measured at a wavelength of 850 nm) in each of Examples 16 to 25 and Comparative Examples 4 to 7.
Figure 8:
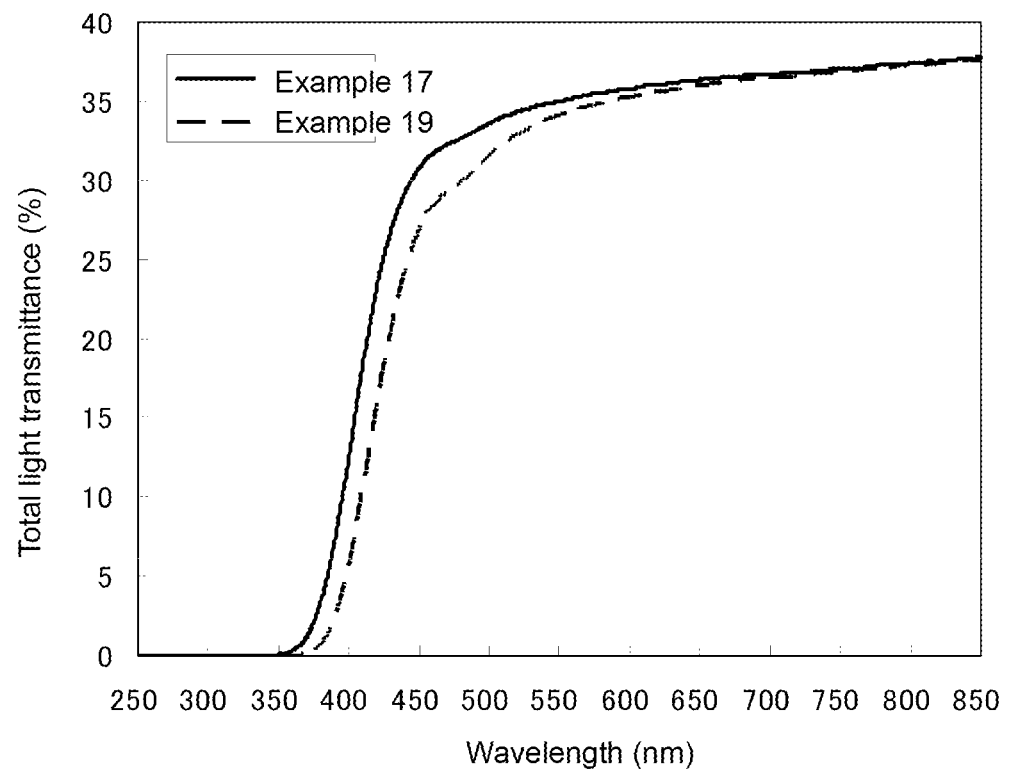
FIG. 8 illustrates the measurement wavelength dependency of the total light transmittance in each of Example 17 and Example 19.

Now, the colored translucent zirconia sintered body of the present invention will be described below.

The present invention relates to a colored translucent zirconia sintered body. Therefore, the sintered body of the present invention is a zirconia polycrystalline form having a color tone other than colorless and having translucency. Accordingly, the colored translucent zirconia sintered body of the present invention is different from a zirconia sintered body which is opaque (hereinafter referred to as an opaque zirconia sintered body) and a zirconia single crystal. Here, the opaque zirconia sintered body is, for example, a zirconia sintered body having a total light transmittance of at most 10% as measured at a sample thickness of 1 mm and with a D65 light source.

The colored translucent zirconia sintered body of the present invention contains an iron compound. The iron compound functions as a coloring agent for coloring. The content of the iron compound is preferably less than 2,000 ppm (0.2 wt %) as calculated as $Fe_2O_3$. When the iron compound content is less than 2,000 ppm, the color tone of the sintered body becomes to a light yellow, whereby a color tone similar to that of natural teeth can be obtained more easily. Further, the absorption of light in a visible wavelength region will be suppressed, whereby the translucency is less likely to be decreased. The colored translucent zirconia sintered body of the present invention has a color tone similar to that of natural teeth by containing an iron compound. Therefore, in the colored translucent zirconia sintered body of the present invention, the lower limit of the iron compound content is not particularly limited so long as an iron compound is contained (that is, the content of an iron compound exceeds 0 ppm as calculated as $Fe_2O_3$). For example, when the content of an iron compound is at least 50 ppm (0.005 wt %) as calculated as $Fe_2O_3$, the colored translucent zirconia sintered body of the present invention has a light color tone similar to that of natural teeth.

Here, the content of an iron compound is a ratio of an iron compound as calculated as $Fe_2O_3$ to the total weight of $ZrO_2$ and $Y_2O_3$ contained in the colored translucent zirconia sintered body (in a case where the colored translucent zirconia sintered body contains alumina, the total weight of $ZrO_2$, $Y_2O_3$ and $Al_2O_3$ contained in the colored translucent zirconia sintered body).

The colored translucent zirconia sintered body of the present invention may contain a compound which forms a solid solution with zirconia, in addition to an iron compound, so as to finely adjust the color tone. The compound which forms a solid solution with zirconia may, for example, be at least one oxide selected from Group 3a (Group 3), Group 5a (Group 5), Group 6a (Group 6), Group 7a (Group 7), Group 8 (Groups 8 to 10) and Group 3b (Group 13) of the Periodic Table (the numbering system approved by the International Union of Pure and Applied Chemistry (IUPAC) is shown in brackets).

The colored translucent zirconia sintered body of the present invention contains from 2 to 4 mol % of yttria. If the yttria content is less than 2 mol %, the crystalline phase contains a monoclinic phase, the strength of the sintered body decreases, and further, the sintered body is susceptible to hydrothermal deterioration and is likely to be broken after using it for a long period of time. On the other hand, if the yttria content exceeds 4 mol %, the strength of the sintered body decreases.

The colored translucent zirconia sintered body of the present invention preferably contains alumina. When the colored translucent zirconia sintered body contains alumina (that is, the content of alumina exceeds 0 wt %), it becomes less susceptible to hydrothermal deterioration. As a result, so-called a "color dropout" phenomenon is less likely to occur, and discoloration or decoloration is less likely to occur even after using it for a long period of time.

When the colored translucent zirconia sintered body of the present invention contains alumina, the content of alumina is preferably less than 0.25 wt %, more preferably at most 0.15 wt %. When the content of alumina is less than 0.25 wt %, a colored translucent zirconia sintered body having high translucency can be obtained. On the other hand, the content of alumina is preferably at least 0.005 wt %, more preferably at least 0.01 wt %, further preferably at least 0.025 wt %. When the content of alumina is at least 0.005 wt %, for example, in an acceleration test such as a hot water treatment, discoloration or decoloration is less likely to occur, whereby the color tone is less likely to change after using it as a dental material for a long period of time.

Here, the content of alumina is a ratio of $Al_2O_3$ to the total weight of $ZrO_2$ and $Y_2O_3$ in the colored translucent zirconia sintered body.

The relative density of the colored translucent zirconia sintered body of the present invention is at least 99.80%, preferably at least 99.85%, more preferably at least 99.90%. If the relative density is less than 99.80%, the translucency tends to decrease, whereby a sintered body having poor aesthetic properties for dental materials will be obtained.

The colored translucent zirconia sintered body of the present invention preferably shows a lightness L* in L*a*b* color system (hereinafter simply referred to as "lightness L*" or "L*") of at least 51 when the content of an iron compound is less than 2,000 ppm. Further, when the content of an iron compound is less than 500 ppm, the lightness L* is preferably more than 70 and at most 80.

The colored translucent zirconia sintered body of the present invention preferably shows a lightness L* of from 51 to 70 and has an iron compound content of at least 500 ppm and less than 2,000 ppm as calculated as $Fe_2O_3$. Further, the colored translucent zirconia sintered body of the present invention preferably shows a lightness L* of more than 70 and at most 80 and has an iron compound content of at least 50 ppm and less than 500 ppm as calculated as $Fe_2O_3$.

By having not only translucency but also showing a lightness L* of within these ranges, the colored translucent zirconia sintered body of the present invention has aesthetic properties equivalent to those of natural teeth. Further, the smaller the value of lightness L*, the lower the total light transmittance.

The colored translucent zirconia sintered body of the present invention has a hue a* in L*a*b* color system (hereinafter simply referred to as "hue a*" or "a*") of preferably from −5 to 10, more preferably from −4 to 9, further preferably from −3 to 8. Further, when the hue a* is within these ranges, the hue b* in L*a*b* color system (hereinafter simply referred to as "hue b*" or "b*") is preferably from 0 to 30, more preferably from 0 to 29, further preferably from 0 to 28.

The color tone of the colored translucent zirconia sintered body of the present invention is defined by the lightness L* and the hue a* and b*. Here, the larger the lightness L*, the lighter the color tone, and on the contrary, the smaller the lightness L*, the darker the color tone. Further, the color tone of the colored translucent zirconia sintered body of the present invention is a value measured by collecting light transmitted through the sintered body and light reflected from the sintered body. Therefore, the color tone changes along with a change in the thickness or the translucency of the sintered body. Accordingly, the color tone of the colored translucent zirconia sintered body of the present invention is a value different from the color tone of an opaque zirconia sintered body having no translucency, i.e. a value obtained from the lightness L* and the hue a* and b* which are measured by collecting light reflected from the surface of the sintered body.

The colored translucent zirconia sintered body of the present invention has a total light transmittance as measured at a sample thickness of 1 mm and with a D65 light source (hereinafter simply referred to as "total light transmittance") of preferably at least 20%, more preferably at least 23%, further preferably at least 25%, when the lightness L* is at least 51 and less than 70. Further, when the lightness L* is more than 70 and at most 80, the total light transmittance is preferably at least 20%, more preferably at least 35%, further preferably at least 40%. When the lightness L* is within the range of the present invention and the total light transmittance is at least 20%, aesthetic properties suitable for various dental materials are likely to be obtained. On the other hand, when its translucency is equivalent to that of natural teeth, its total light transmittance is not required to be higher than necessary. For example, when the total light transmittance is at most 43%, a translucency equivalent to that of natural teeth can be obtained.

The colored translucent zirconia sintered body of the present invention has a total light transmittance as measured at a sample thickness of 1 mm and a wavelength of 850 nm (hereinafter referred to as "near-infrared transmittance") of preferably at least 35%, more preferably at least 35.5%, further preferably at least 36%. When the near-infrared transmittance is at least 35%, a material suitable not only for dental materials, which are required to have an aesthetic translucency, but also for a protection layer of an energy conversion material (e.g. solar cell) or the like, will be obtained. The near-infrared transmittance of the colored translucent zirconia sintered body of the present invention is high, whereby a sintered body having a near-infrared transmittance of around 40% can be obtained.

The colored translucent zirconia sintered body of the present invention preferably contains tetragonal phase in its crystalline phase, and preferably has a crystalline phase constituted only of tetragonal phase. Thus, the mechanical strength tends to be high. The colored translucent zirconia sintered body of the present invention has a three-point bending strength of preferably at least 1,000 MPa, more preferably at least 1,100 MPa, further preferably at least 1,200 MPa.

Further, the crystal grain size of the colored translucent zirconia sintered body of the present invention is preferably from 0.2 µm to 0.45 µm, more preferably from 0.3 µm to 0.45 µm. When the crystal grain size is 0.2 µm or larger, pores are less likely to remain in the sintered body, whereby the relative density tends to be high. Further, when the crystal grain size is at most 0.45 µm, the hydrothermal deterioration of the sintered body tends to be suppressed, whereby it can be used as a dental material for a long period of time.

The colored translucent zirconia sintered body of the present invention has a monoclinic phase transformation depth after immersion in a hot water of 140° C. for 24 hours of preferably at most 20 µm, more preferably at most 10 µm. The monoclinic phase transformation depth can be used as an index of deterioration of the zirconia sintered body under a hydrothermal environment. That is, a small monoclinic phase transformation depth is an index indicating that deterioration is less likely occur after using it as a dental material for a long period of time. When the monoclinic phase transformation depth is at most 20 µm, the hydrothermal deterioration of the sintered body is less likely to proceed, whereby the sintered body is less likely to be broken. The monoclinic phase transformation depth can be measured by observing the cross section of the sintered body with a scanning electron microscope (SEM), etc.

Further, the colored translucent zirconia sintered body of the present invention has a monoclinic phase transformation depth after immersion in a hot water of 140° C. for 72 hours of preferably at most 20 µm, more preferably at most 10 µm.

The colored translucent zirconia sintered body of the present invention has a monoclinic phase ratio after immersion in a hot water of 140° C. for 24 hours of preferably at most 30%, more preferably at most 15%.

Further, the colored translucent zirconia sintered body of the present invention has a monoclinic phase ratio after immersion in a hot water of 140° C. for 72 hours of preferably at most 80%, more preferably at most 60%.

Here, the monoclinic phase ratio (also referred to as M phase ratio) is a value calculated based on the following expression 1 after carrying out a XRD measurement with regard to a mirror-polished portion of the sintered body, and obtaining the diffraction intensities of each of the (111) and (11-1) phase of a monoclinic phase, the (111) phase of a tetragonal phase, and the (111) phase of a cubic phase.

$$f_m(\%) = \frac{I_m(111) + I_m(11-1)}{I_m(111) + I_m(11-1) + I_t(111) + I_c(111)} \times 100 \quad \text{[Expression 1]}$$

Now, the process for producing the colored translucent zirconia sintered body of the present invention will be described.

The colored translucent zirconia sintered body of the present invention can be produced by molding and sintering of a mixed powder comprised of a zirconia powder and an iron compound.

The zirconia powder has a BET specific surface area of preferably from 10 m$^2$/g to 15 m$^2$/g, more preferably from 11 m$^2$/g to 14 m$^2$/g. When the BET specific surface area of the zirconia powder is at least 10 m$^2$/g, a powder which is easily sintered even at a low temperature will be obtained. Further, when the BET specific surface area is at most 15 m$^2$/g, a powder which is less likely to aggregate with other powders will be obtained.

The zirconia powder has an average particle size of preferably from 0.4 μm to 0.7 μm, more preferably from 0.4 μm to 0.6 μm. When the average particle size of the zirconia powder is at least 0.4 μm, the amount of fine particles which cause aggregation of the powder becomes low, whereby molding is easy. On the other hand, when the average particle size is at most 0.7 μm, the amount of coarse particles including hard agglomerated particles becomes low, whereby molding is easy. Further, since coarse particles inhibit densification of a sintered body and deteriorate sintering property, the maximum particle size of the zirconia powder is preferably at most 2.0 μm, more preferably at most 1.5 μm.

The zirconia powder has, in the air, a sintering shrinkage rate ($\Delta\rho/\Delta T$:g/cm$^3$·°C.) during relative densities of from 70% to 90% (hereinafter simply referred to as "sintering shrinkage rate") of preferably from 0.012 to 0.016, when it is sintered under normal pressure with a temperature-rising rate of 300° C./hr. The sintering shrinkage rate is an index for the sintering property of the zirconia powder. When the sintering shrinkage rate is within this range, a zirconia powder having an excellent sintering property will be obtained. Further, the sintering shrinkage rate is a value measured at a relative density of at least 70%. Therefore, the sintering shrinkage rate is not affected by fluctuations in the density of the green body. Further, during relative densities of from 70% to 90%, the sintering shrinkage proceeds at a constant rate. Accordingly, the shrinkage rate is a linear function of the temperature and the relative density, and therefore it is possible to obtain an accurate shrinkage rate without using a special approximation process.

The zirconia powder is preferably a zirconia powder obtained by subjecting a hydrated zirconia sol, which is obtained by the hydrolysis of a zirconium salt aqueous solution, to drying, calcination, and crushing.

The zirconium salt to be used for the preparation of the hydrated zirconia sol may be at least one of zirconium oxychloride, zirconyl nitrate, zirconium chloride, zirconium sulfate, and a mixture of zirconium hydroxide and an acid. Further, in the zirconium salt aqueous solution, an alkali metal hydroxide or an alkaline earth metal hydroxide, or both of them (hereinafter referred to as "alkali metal hydroxide or the like") may be added. The alkali metal hydroxide or the like may, for example, be an hydroxide of lithium, sodium, potassium, magnesium or calcium.

When the hydrated zirconia sol as obtained above is dried and calcinated, a calcined zirconia powder can be obtained. The calcination temperature is preferably from 1,000 to 1,200° C., more preferably from 1,050 to 1,150° C. When the calcination is carried out under these temperature ranges, the aggregation property of the calcined zirconia powder tends to be decreased, and further the amount of coarse particles including aggregated particles tends to be decreased. Accordingly, the average particle size of the zirconia powder after crushing tends to be from 0.4 μm to 0.7 μm.

Thereafter, by crushing the calcined zirconia powder as obtained above, a zirconia powder can be obtained. The method of crushing is not particularly limited so long as it is carried out in a manner such that the average particle size becomes from 0.4 μm to 0.7 μm. The method of crushing is preferably a wet-crushing using zirconia balls.

For the colored translucent zirconia sintered body of the present invention, a mixed powder is obtained by mixing the zirconia powder and an iron compound.

The types of the iron compound may, for example, be a water-soluble compound such as iron chloride or iron nitrate, and a water-insoluble compound such as iron oxide or iron oxide hydroxide.

When the water-insoluble compound is used, it is preferred to mix an iron compound having an average particle size of at most 1 μm at the time of crushing the calcined zirconia powder, whereby the aggregates of the water-insoluble iron compound disappear and the color tone of the obtained sintered body tends to be homogeneous.

The amount of the iron compound to be mixed is, based on the total weight of ZrO$_2$ and Y$_2$O$_3$ (when adding alumina, the total weight of ZrO$_2$, Y$_2$O$_3$ and Al$_2$O$_3$), preferably less than 2,000 ppm (0.2 wt %), more preferably at most 1,800 ppm (0.18 wt %), further preferably at most 1,600 ppm (0.16 wt %), as calculated as Fe$_2$O$_3$.

When the colored translucent zirconia sintered body of the present invention contains alumina, the alumina source is added in an amount of preferably less than 0.25 wt %, more preferably at most 0.15 wt %, based on the total weight of ZrO$_2$ and Y$_2$O$_3$.

The alumina source may, for example, be at least any one of alumina, hydrated alumina, alumina sol, aluminum hydroxide, aluminum chloride, aluminum nitrate and aluminum sulfate. The alumina source is preferably a water-insoluble alumina compound, more preferably alumina.

The mixed powder is obtained by mixing the zirconia powder, the iron compound and, as the case requires, the alumina source. Accordingly, the composition of the mixed powder is equivalent to the composition of the colored translucent zirconia sintered body obtained therefrom.

The zirconia powder or the mixed powder is preferably used as spray-granulation powder granules prepared by spray drying after transforming it into a slurry. As a result, the fluidity of the powder at the time of forming a green body increases, whereby the pores are likely to be removed from the green body.

The spray granulation powder granules preferably have a particle size of from 30 μm to 80 μm, and an untamped density of from 1.10 g/cm$^3$ to 1.40 g/cm$^3$.

The colored translucent zirconia sintered body of the present invention can be produced by molding the mixed powder to form a green body, and then sintering the green body.

The molding method is not particularly limited so long as the green body has a relative density of around 50±5%. The molding method is preferably a method wherein a mixed powder is subjected to a press-molding and then, as the case requires, subjected to a cold isostatic pressing (hereinafter referred to as "CIP").

The colored translucent zirconia sintered body of the present invention can be obtained by sintering the obtained green body.

The sintering method is preferably a sintering method carried out under normal pressure, i.e. a so-called normal pressure sintering. Particularly, when the zirconia powder obtained by the above method is used, a colored zirconia sintered body having high strength and translucency can be obtained only by the normal pressure sintering without carrying out a hot isostatic pressing (hereinafter referred to as "HIP").

The sintering temperature is preferably from 1,350 to 1,450° C., more preferably from 1,400 to 1,450° C. When the sintering temperature is at least 1,350° C., the relative density tends to be high as 99.80%. On the other hand, when the sintering temperature is at most 1,450° C., the hydrothermal deterioration is less likely to occur, whereby a sintered body which can be used as a dental material for a long period of time will be obtained.

The sintering atmosphere is preferably an atmosphere other than a reducing atmosphere, and is preferably an oxygen atmosphere or the air. For the simplicity, the sintering is preferably carried out in the air.

EXAMPLES

Now, the present invention will be described in detail with reference to Examples. However, the present invention is not construed as being limited to the Examples.

(Measurement of Sintering Shrinkage Rate)

The sintering shrinkage rate of a mixed powder was measured as follows. The mixed powder was molded by a press molding using a metallic mold, and then subjected to CIP treatment at a pressure of 2 t/cm$^2$, thereby to obtain a green body having a relative density of 50±5%. The obtained green body was sintered under normal pressure, in the air, with a temperature-rising rate of 300° C./hr and at a temperature of 1,500° C., to measure its heat shrinkage behavior. For the measurement, a conventional thermal dilatometer (manufactured by ULVAC-RIKO, model name: DL9700) was used.

From the obtained heat shrinkage behavior, the temperature at which the relative density changes from 70% to 90% was obtained, thereby to obtain the heat shrinkage rate.

(Measurement of Average Particle Size)

The average particle size of the zirconia powder was measured by using a MICROTRAC particle size distribution analyzer (manufactured by Honeywell, model name: 9320-HRA). The median of the cumulative curve of the particle size distribution represented by a volume basis (median size; particle size corresponds to 50% of the cumulative curve) was used as an average particle size.

Prior to the measurement, the powder was suspended in distilled water, and then dispersed for 3 minutes by using a ultrasonic homogenizer (manufactured by Nippon Seiki Seisakusho, model name: US-150T) to carry out a pre-treatment.

(Measurement of Density ρ of the Green Body or the Sintered Body (Hereinafter Referred to as "Measured Density"))

The size of the green body was measured by using a caliper to obtain the volume of the green body, and then the measured density of the green body was calculated from the obtained volume and the weight of the green body. Further, the measured density of the sintered body was calculated by Archimedes' method.

(Measurement of Relative Density)

The relative density was calculated from theoretical density $\rho_0$ and measured density $\rho$ by using the following formula (1).

$$\text{Relative density}(\%) = (\rho/\rho_0) \times 100 \quad (1)$$

Further, theoretical density $\rho_0$ was calculated by using the following formula (2).

$$\rho_0 = 100/[(X/\rho_{Al}) + (Y/\rho_{Fe}) + (100 - X - Y)/\rho_{Zr}] \quad (2)$$

X: alumina content; wt %
Y: $Fe_2O_3$ content; wt %
$\rho_{Al}$: theoretical density of alumina; 3.987 g/cm$^3$
$\rho_{Zr}$: theoretical density of zirconia; 6.0956 g/cm$^3$
$\rho_{Fe}$: theoretical density of $Fe_2O_3$; 5.24 g/cm$^3$ (Measurement of Total Light Transmittance and Near-Infrared Transmittance)

The total light transmittance was measured in accordance with JIS K7361 by using a turbidity meter (manufactured by Nippon Denshoku Industries Co., Ltd., model name: NDH2000). Light source D65 was used as the light source. The measurement was carried out by using a sample having a disk shape and a thickness of 1 mm obtained by polishing the both surfaces of a sintered body.

Further, the near-infrared transmittance (total light transmittance as measured at a wavelength of 850 nm) was measured by using a ultraviolet visible near-infrared spectrophotometer (manufactured by JASCO Corporation, model name: V-650) equipped with an integrating sphere unit having a diameter of 150 mm (model name: ILV-724). The measurement was carried out by using a sample having a disk shape and a thickness of 1 mm obtained by polishing the both surfaces of a sintered body.

(Measurement of Color Tone)

The lightness L*, hue a* and b* were measured in accordance with JIS Z8729. For the measurement of the color tone, a sample having a thickness of 2.8 mm, a disk shape, and one mirror-polished surface was used. The measurement was carried out with regard to the mirror-polished surface.

(Measurement of Strength of Sintered Body)

The strength of a sintered body was measured in accordance with JIS R1601, and evaluated by a three-point bending measurement method.

(Measurement of Crystal Grain Size)

The crystal grain size of a zirconia sintered body was calculated by the planimetric method from a picture of a scanning electron microscope (SEM) observation, after subjecting the mirror-polished sintered body to a heat etching treatment. Specifically, a circle was drawn on the microscopic image so that the total of the number of particles inside circle $n_c$ and the number of particles on the circle $N_i$ becomes from 100 to 150, or a plurality of circles was drawn on a plurality of microscopic images so that the total of the number of particles $(n_c + N_i)$ becomes from 100 to 150 when the number of particles on a single image was less than 100, thereby to obtain the crystal grain size by the planimetric method.

(Hydrothermal Deterioration Properties)

The hydrothermal deterioration properties were evaluated after polishing the obtained sintered body until its one surface became a mirror surface, and then immersing it in a hot water of 140° C. for 24 hours or for 72 hours, to obtain a ratio of the generated monoclinic phase (monoclinic phase ratio). The monoclinic phase ratio (M phase ratio) is a value calculated based on the following expression 1 after carrying out a XRD measurement with regard to a mirror-polished portion of the sintered body subjected to the immersion treatment, and obtaining the diffraction intensities of each of the (111) and (11-1) phase of a monoclinic phase, the (111) phase of a tetragonal phase, and the (111) phase of a cubic phase.

$$f_m(\%) = \frac{I_m(111) + I_m(11-1)}{I_m(111) + I_m(11-1) + I_t(111) + I_c(111)} \times 100 \quad \text{[Expression 2]}$$

Further, the transformation depth was obtained by cutting the immersion-treated sintered body, observing the cross section with a scanning electron microscope (SEM), and measuring the depth at which the crystal organization became rough from the mirror-polished surface.

Example 1

To a zirconium oxychloride aqueous solution, yttrium chloride was added to a $Y_2O_3$ concentration of 3 mol %, and then a hydrated zirconia sol was obtained by hydrolysis. After drying the hydrated zirconia sol, calcining was carried out at a temperature of 1,100° C. for 2 hours, thereby to obtain a calcined zirconia powder containing 3 mol % of yttria.

After washing the obtained calcined zirconia powder with water, α-alumina was mixed therewith to an alumina content of 0.05 wt % based on the calcined zirconia powder. Further, iron hydroxide oxide (FeOOH) was mixed therewith to 1,700 ppm as calculated as $Fe_2O_3$ based on the total weight of the calcined zirconia powder and α-alumina.

After mixing these raw materials, distilled water was added to obtain a slurry having a zirconia concentration of 45 wt %. The slurry was milled for 24 hours with a vibration mill using a zirconia ball having a diameter of 3 mm to obtain a milled slurry. Further, a part of the milled slurry was dried to obtain a mixed powder for measuring BET specific surface area.

The average particle size and the maximum particle size of the particles contained in the milled slurry were found to be 0.43 μm and 1.16 μm, respectively. The BET specific surface area of the mixed powder was found to be 12.5 m²/g.

To the obtained milled slurry, an organic binder was added in an amount of 3 wt %, and then a spray-drying was carried out to obtain a zirconia powder having an average particle size of from 45 to 50 μm.

The obtained zirconia powder was subjected to a uniaxial pressing at a pressure of 19.6 MPa, followed by CIP treatment at a pressure of 196 MPa to obtain a green body.

The obtained green body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 600° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

Example 2

A colored translucent zirconia sintered body was obtained in the same manner as in Example 1 except that the sintering temperature was changed to 1,450° C. Results are shown in Table 1.

Reference Example

The colored translucent zirconia sintered body obtained in Example 2 was subjected to a hot isostatic pressing (HIP) treatment at a treatment temperature of 1,400° C. and a pressure of 150 MPa.

Little changes in the relative density and L* value of the colored translucent zirconia sintered body were found through the HIP treatment. As a result, the colored translucent zirconia sintered body of the present invention was found to be a sintered body having properties equivalent to ones obtained after HIP treatment without carrying out HIP treatment.

Example 3

A colored translucent zirconia sintered body was obtained in the same manner as in Example 1 except that 1,500 ppm of iron hydroxide oxide as calculated as $Fe_2O_3$ was added. The results are shown in Table 1.

Example 4

A colored translucent zirconia sintered body was obtained in the same manner as in Example 1 except that 1,500 ppm of iron hydroxide oxide as calculated as $Fe_2O_3$ was added and the sintering temperature was changed to 1,450° C. The results are shown in Table 1.

Example 5

A colored translucent zirconia sintered body was obtained in the same manner as in Example 1 except that 750 ppm of iron hydroxide oxide as calculated as $Fe_2O_3$ was added. The results are shown in Table 1.

Example 6

A colored translucent zirconia sintered body was obtained in the same manner as in Example 1 except that 750 ppm of iron hydroxide oxide as calculated as $Fe_2O_3$ was added and the sintering temperature was changed to 1,450° C. The results are shown in Table 1.

Example 7

A colored translucent zirconia sintered body was obtained in the same manner as in Example 1 except that 0.1 wt % of α-alumina in terms of alumina content was added, 1,500 ppm of iron hydroxide oxide as calculated as $Fe_2O_3$ was added, and the sintering temperature was changed to 1,450° C. The results are shown in Table 1.

Example 8

A colored translucent zirconia sintered body was obtained in the same manner as in Example 1 except that 0.1 wt % of α-alumina in terms of alumina content was added and 750 ppm of iron hydroxide oxide as calculated as $Fe_2O_3$ was added. The results are shown in Table 1.

Example 9

A colored translucent zirconia sintered body was obtained in the same manner as in Example 1 except that 0.15 wt % of α-alumina in terms of alumina content was added and 1,500 ppm of iron hydroxide oxide as calculated as $Fe_2O_3$ was added. The results are shown in Table 1.

Example 10

A colored translucent zirconia sintered body was obtained in the same manner as in Example 1 except that 0.15 wt % of α-alumina in terms of alumina content was added and 750 ppm of iron hydroxide oxide as calculated as $Fe_2O_3$ was added. The results are shown in Table 1.

Example 11

A colored translucent zirconia sintered body was obtained in the same manner as in Example 1 except that 500 ppm of iron hydroxide oxide as calculated as $Fe_2O_3$ was added. The results are shown in Table 1.

Example 12

A colored translucent zirconia sintered body was obtained in the same manner as in Example 1 except that 500 ppm of iron hydroxide oxide as calculated as $Fe_2O_3$ was added and the sintering temperature was changed to 1,450° C. The results are shown in Table 1.

Comparative Example 1

A colored translucent zirconia sintered body was obtained in the same manner as in Example 1 except that no α-alumina was added, 1,500 ppm of iron hydroxide oxide as calculated as $Fe_2O_3$ was added, and the sintering temperature was changed to 1,450° C. The results are shown in Table 1.

Comparative Example 2

A colored translucent zirconia sintered body was obtained in the same manner as in Example 1 except that 0.25 wt % of α-alumina in terms of alumina content was added and 2,000 ppm of iron hydroxide oxide as calculated as $Fe_2O_3$ was added. The results are shown in Table 1.

Comparative Example 3

A colored translucent zirconia sintered body was obtained in the same manner as in Example 1 except that 0.25 wt % of α-alumina in terms of alumina content was added, 2,000 ppm of iron hydroxide oxide as calculated as $Fe_2O_3$ was added, and the sintering temperature was changed to 1,450° C. The results are shown in Table 1.

Example 13

A mixed powder was obtained in the same manner as in Example 1 except that 1,350 ppm of iron hydroxide oxide as calculated as $Fe_2O_3$ was added. The obtained mixed powder was subjected to a uniaxial press molding at a pressure of 49.0 MPa, followed by CIP treatment at a pressure of 196 MPa to obtain a green body.

The obtained green body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 400° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

Example 14

A colored translucent zirconia sintered body was obtained in the same manner as in Example 13 except that 700 ppm of iron hydroxide oxide as calculated as $Fe_2O_3$ was added. The results are shown in Table 1.

Example 15

41% of the mixed powder obtained in Example 1 by adding 1,700 ppm of iron hydroxide oxide as calculated as $Fe_2O_3$, and 59% of a powder obtained in the same manner as in Example 1 except that no iron hydroxide oxide was added therein (calcined zirconia powder+α-alumina) were mixed in a plastic bottle to obtain a mixed powder containing 700 ppm of iron hydroxide oxide as calculated as $Fe_2O_3$.

The obtained mixed powder was subjected to a uniaxial press molding at a pressure of 49.0 MPa, followed by CIP treatment at a pressure of 196 MPa to obtain a molded body.

The obtained molded body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 400° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

Example 16

To a zirconium oxychloride aqueous solution, yttrium chloride was added to a $Y_2O_3$ concentration of 3 mol %, and then a hydrated zirconia sol was obtained by hydrolysis. After drying the hydrated zirconia sol, calcining was carried out at a temperature of 1,100° C. for 2 hours, thereby to obtain a calcined zirconia powder containing 3 mol % of yttria.

After washing the obtained calcined zirconia powder with water, α-alumina was mixed therewith to an alumina content of 0.05 wt % based on the calcined zirconia powder. Further, iron hydroxide oxide (FeOOH) was mixed therewith to 200 ppm as calculated as $Fe_2O_3$ based on the total weight of the calcined zirconia powder and α-alumina.

After mixing these raw materials, distilled water was added to obtain a slurry having a zirconia concentration of 45 wt %. The slurry was milled for 24 hours with a vibration mill using a zirconia ball having a diameter of 3 mm to obtain a milled slurry. Further, a part of the milled slurry was dried to obtain a mixed powder for measuring BET specific surface area.

The average particle size and the maximum particle size of the particles contained in the milled slurry were found to be 0.44 μm and 1.38 μm, respectively. The BET specific surface area of the mixed powder was found to be 12.3 $m^2/g$.

To the obtained milled slurry, an organic binder was added in an amount of 3 wt %, and then a spray-drying was carried out to obtain a zirconia powder having an average particle size of from 45 to 50 μm.

The obtained zirconia powder was subjected to a uniaxial pressing at a pressure of 19.6 MPa, followed by CIP treatment at a pressure of 196 MPa to obtain a green body.

The obtained green body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 600° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

Example 17

A colored translucent zirconia sintered body was obtained in the same manner as in Example 16 except that the sintering temperature was changed to 1,450° C. Results are shown in Table 1.

Example 18

A colored translucent zirconia sintered body was obtained in the same manner as in Example 16 except that 80 ppm of iron hydroxide oxide as calculated as $Fe_2O_3$ was added. The results are shown in Table 1.

Example 19

A colored translucent zirconia sintered body was obtained in the same manner as in Example 16 except that 80 ppm of iron hydroxide oxide as calculated as $Fe_2O_3$ was added and the sintering temperature was changed to 1,450° C. The results are shown in Table 1.

Example 20

A colored translucent zirconia sintered body was obtained in the same manner as in Example 16 except that 0.1 wt % of α-alumina in terms of alumina content was added. The results are shown in Table 1.

Example 21

A colored translucent zirconia sintered body was obtained in the same manner as in Example 16 except that 0.15 wt % of α-alumina in terms of alumina content was added. The results are shown in Table 1.

Example 22

A colored translucent zirconia sintered body was obtained in the same manner as in Example 16 except that no α-alumina was added and the sintering temperature was changed to 1,450° C. The results are shown in Table 1.

Comparative Example 4

A colored translucent zirconia sintered body was obtained in the same manner as in Example 16 except that 0.25 wt % of α-alumina in terms of alumina content was added and 1,000 ppm of iron hydroxide oxide as calculated as $Fe_2O_3$ was added. The results are shown in Table 1.

Comparative Example 5

A colored translucent zirconia sintered body was obtained in the same manner as in Example 16 except that 0.25 wt % of α-alumina in terms of alumina content was added and 500 ppm of iron hydroxide oxide as calculated as $Fe_2O_3$ was added. The results are shown in Table 1.

Comparative Example 6

A colored translucent zirconia sintered body was obtained in the same manner as in Example 16 except that 0.25 wt % of α-alumina in terms of alumina content was added, 1,000 ppm of iron hydroxide oxide as calculated as $Fe_2O_3$ was added, and the sintering temperature was changed to 1,450° C. The results are shown in Table 1.

Comparative Example 7

A colored translucent zirconia sintered body was obtained in the same manner as in Example 16 except that 0.25 wt % of α-alumina in terms of alumina content was added, 500 ppm of iron hydroxide oxide as calculated as $Fe_2O_3$ was added, and the sintering temperature was changed to 1,450° C. The results are shown in Table 1.

Example 23

A mixed powder was obtained in the same manner as in Example 16.

The obtained mixed powder was subjected to a uniaxial press molding at a pressure of 49.0 MPa, followed by CIP treatment at a pressure of 196 MPa to obtain a green body.

The obtained green body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 400° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

Example 24

A colored translucent zirconia sintered body was obtained in the same manner as in Example 23 except that 80 ppm of iron hydroxide oxide as calculated as $Fe_2O_3$ was added. The results are shown in Table 1.

Example 25

12% of the mixed powder obtained in Example 1 by adding 1,700 ppm of iron hydroxide oxide as calculated as $Fe_2O_3$, and 88% of a powder obtained in the same manner as in Example 1 except that no iron hydroxide oxide was added therein (calcined zirconia powder+α-alumina) were mixed in a plastic bottle to obtain a mixed powder containing 200 ppm of iron hydroxide oxide as calculated as $Fe_2O_3$.

The obtained mixed powder was subjected to a uniaxial press molding at a pressure of 49.0 MPa, followed by CIP treatment at a pressure of 196 MPa to obtain a green body.

The obtained green body was, in the air, heated to 1,000° C. with a temperature-rising rate of 50° C./hr, and retained for 1 hour to remove the binder. Thereafter, in the air, atmospheric sintering was carried out at a sintering temperature of 1,400° C., with a temperature-rising rate of 400° C./hr, and retained for 2 hours at the sintering temperature, thereby to obtain a colored translucent zirconia sintered body. The obtained colored translucent zirconia sintered body was found to have a crystalline phase constituted only of tetragonal phase. The results are shown in Table 1.

TABLE 1

| | $Al_2O_3$ (wt %) | $Fe_2O_3$ (ppm) | Δρ/ΔT (g/cm³ · ° C.) | Sintering temperature (° C.) | Relative density (%) | Total light transmittance (%; D65) | Near-infrared transmittance (%; 850 nm) |
|---|---|---|---|---|---|---|---|
| Ex. 1 | 0.05 | 1700 | 0.0155 | 1400 | 99.89 | 20.5 | 35.4 |
| Ex. 2 | 0.05 | 1700 | 0.0155 | 1450 | 99.90 | 22.2 | 35.4 |

TABLE 1-continued

|  |  |  |  |  |  |  |  |
|---|---|---|---|---|---|---|---|
| Ref. Ex. | 0.05 | 1700 | 0.0155 | 1450 + HIP | 99.94 | 24.6 | 35.3 |
| Ex. 3 | 0.05 | 1500 | 0.0154 | 1400 | 99.91 | 23.6 | 36.3 |
| Ex. 4 | 0.05 | 1500 | 0.0154 | 1450 | 99.91 | 25.6 | 35.9 |
| Ex. 5 | 0.05 | 750 | 0.0155 | 1400 | 99.90 | 33.1 | 37.5 |
| Ex. 6 | 0.05 | 750 | 0.0155 | 1450 | 99.92 | 34.5 | 37.1 |
| Ex. 7 | 0.10 | 1500 | 0.0158 | 1400 | 99.88 | 26.8 | 36.4 |
| Ex. 8 | 0.10 | 750 | 0.0159 | 1400 | 99.91 | 33.9 | 37.3 |
| Ex. 9 | 0.15 | 1500 | 0.0164 | 1400 | 99.89 | 28.5 | 36.1 |
| Ex. 10 | 0.15 | 750 | 0.0165 | 1400 | 99.92 | 34.9 | 37.1 |
| Ex. 11 | 0.05 | 500 | 0.0154 | 1400 | 99.91 | 36.8 | 38.0 |
| Ex. 12 | 0.05 | 500 | 0.0154 | 1450 | 99.91 | 37.5 | 37.8 |
| Comp. Ex. 1 | 0 | 1500 | 0.0145 | 1450 | 99.88 | 15.3 | 35.2 |
| Comp. Ex. 2 | 0.25 | 2000 | 0.0172 | 1400 | 99.67 | 14.1 | 29.0 |
| Comp. Ex. 3 | 0.25 | 2000 | 0.0172 | 1450 | 99.75 | 18.1 | 32.5 |
| Ex. 13 | 0.05 | 1350 | 0.0154 | 1400 | 99.89 | 21.9 | 35.5 |
| Ex. 14 | 0.05 | 700 | 0.0155 | 1400 | 99.90 | 32.0 | 37.1 |
| Ex. 15 | 0.05 | 700 | 0.0154 | 1400 | 99.90 | 32.1 | 37.3 |
| Ex. 16 | 0.05 | 200 | 0.0154 | 1400 | 99.91 | 40.8 | 38.1 |
| Ex. 17 | 0.05 | 200 | 0.0154 | 1450 | 99.91 | 40.8 | 37.5 |
| Ex. 18 | 0.05 | 80 | 0.0154 | 1400 | 99.91 | 42.0 | 38.1 |
| Ex. 19 | 0.05 | 80 | 0.0154 | 1450 | 99.91 | 41.9 | 37.7 |
| Ex. 20 | 0.10 | 200 | 0.0159 | 1400 | 99.93 | 40.0 | 37.8 |
| Ex. 21 | 0.15 | 200 | 0.0164 | 1400 | 99.94 | 40.3 | 37.7 |
| Ex. 22 | 0 | 200 | 0.0145 | 1450 | 99.86 | 39.1 | 38.1 |
| Comp. Ex. 4 | 0.25 | 1000 | 0.0171 | 1400 | 99.70 | 20.5 | 28.8 |
| Comp. Ex. 5 | 0.25 | 500 | 0.0171 | 1400 | 99.77 | 24.4 | 28.3 |
| Comp. Ex. 6 | 0.25 | 1000 | 0.0171 | 1450 | 99.78 | 26.8 | 33.1 |
| Comp. Ex. 7 | 0.25 | 500 | 0.0171 | 1450 | 99.77 | 30.9 | 34.1 |
| Ex. 23 | 0.05 | 200 | 0.0154 | 1400 | 99.90 | 39.4 | 37.2 |
| Ex. 24 | 0.05 | 80 | 0.0154 | 1400 | 99.89 | 40.6 | 37.5 |
| Ex. 25 | 0.05 | 200 | 0.0155 | 1400 | 99.90 | 39.6 | 37.3 |

|  |  |  |  |  | Crystal grain size (μm) | Hydrothermal deterioration properties | | | |
|---|---|---|---|---|---|---|---|---|---|
|  |  |  |  |  |  | 140° C. × 24 hr | | 140° C. × 72 hr | |
|  | L* | a* | b* | Strength (MPa) |  | M phase ratio (%) | Transformation depth (μm) | M phase ratio (%) | Transformation depth (μm) |
| Ex. 1 | 56.9 | 7.0 | 27.4 | 1280 | 0.39 | 13 | 6 | 76 | 10 |
| Ex. 2 | 55.7 | 7.9 | 28.2 | — | 0.41 | 76 | 10 | 82 | 33 |
| Ref. Ex. | 56.1 | 6.3 | 27.4 | — | 0.42 | 80 | 12 | 83 | 38 |
| Ex. 3 | 55.9 | 6.7 | 26.8 | 1160 | 0.39 | 13 | 6 | 74 | 9 |
| Ex. 4 | 57.4 | 5.7 | 26.5 | 1130 | 0.41 | 77 | 7 | 80 | 31 |
| Ex. 5 | 64.7 | 1.5 | 20.4 | 1170 | 0.39 | 18 | 9 | 70 | 10 |
| Ex. 6 | 65.7 | 0.8 | 19.5 | 1110 | 0.41 | 79 | 8 | 81 | 32 |
| Ex. 7 | 60.3 | 4.6 | 26.0 | 1170 | 0.39 | 18 | 9 | 82 | 11 |
| Ex. 8 | 67.3 | 0.8 | 20.1 | 1220 | 0.38 | 28 | 10 | 83 | 11 |
| Ex. 9 | 63.1 | 3.4 | 26.1 | — | 0.40 | 5 | 2 | 37 | 8 |
| Ex. 10 | 69.0 | −0.2 | 19.1 | 1240 | 0.39 | 4 | 2 | 73 | 8 |
| Ex. 11 | 69.9 | −0.4 | 15.9 | — | 0.39 | 15 | 8 | 66 | 9 |
| Ex. 12 | 69.9 | −1.2 | 14.0 | — | 0.41 | 78 | 9 | 82 | 35 |
| Comp. Ex. 1 | 50.7 | 9.1 | 27.5 | 1030 | 0.42 | 81 | 18 | 84 | 41 |
| Comp. Ex. 2 | 67.7 | 6.7 | 28.3 | — | 0.38 | 6 | 5 | 73 | 6 |
| Comp. Ex. 3 | 66.2 | 5.2 | 28.1 | 1280 | 0.38 | 12 | 6 | 32 | 8 |
| Ex. 13 | 57.6 | 6.7 | 27.2 | 1130 | 0.38 | 11 | 5 | 56 | 6 |
| Ex. 14 | 66.3 | 1.6 | 20.9 | 1160 | 0.39 | 10 | 5 | 38 | 6 |
| Ex. 15 | 66.1 | 1.4 | 21.0 | 1180 | 0.39 | 10 | 5 | 36 | 6 |
| Ex. 16 | 71.9 | −3.0 | 6.7 | — | 0.39 | 20 | 10 | 75 | 10 |
| Ex. 17 | 71.9 | −2.9 | 6.5 | 1180 | 0.41 | 83 | 13 | 83 | 32 |
| Ex. 18 | 72.7 | −2.8 | 1.7 | — | 0.39 | 18 | 6 | 66 | 7 |
| Ex. 19 | 73.3 | −2.7 | 1.7 | 1170 | 0.41 | 83 | 9 | 83 | 34 |
| Ex. 20 | 72.4 | −2.8 | 7.4 | 1220 | 0.39 | 14 | 13 | 78 | 15 |
| Ex. 21 | 74.5 | −2.8 | 7.7 | — | 0.39 | 30 | 3 | 81 | 8 |
| Ex. 22 | 73.2 | −2.8 | 7.4 | 1050 | 0.42 | 83 | 12 | 84 | 31 |
| Comp. Ex. 4 | 75.9 | 1.7 | 21.5 | — | 0.38 | 11 | 5 | 82 | 6 |

TABLE 1-continued

| | | | | | | | | | |
|---|---|---|---|---|---|---|---|---|---|
| Comp. Ex. 5 | 80.4 | −1.0 | 14.7 | — | 0.38 | 20 | 5 | 83 | 6 |
| Comp. Ex. 6 | 74.1 | 1.1 | 21.0 | — | 0.41 | 11 | 6 | 80 | 10 |
| Comp. Ex. 7 | 78.5 | −1.5 | 13.0 | 1280 | 0.41 | 15 | 5 | 81 | 13 |
| Ex. 23 | 73.1 | −3.0 | 7.0 | 1190 | 0.39 | 7 | 5 | 18 | 6 |
| Ex. 24 | 74.3 | −2.8 | 1.6 | 1170 | 0.38 | 8 | 5 | 22 | 6 |
| Ex. 25 | 73.3 | −2.9 | 6.9 | 1180 | 0.39 | 8 | 5 | 19 | 6 |

The colored translucent zirconia sintered body obtained in each Example is an excellent colored translucent zirconia sintered body having a high relative density and total light transmittance, and can be used as a dental material such as a mill blank or an orthodontic bracket.

INDUSTRIAL APPLICABILITY

The colored translucent zirconia sintered body of the present invention has high strength and aesthetic properties quite similar to the color tone of natural teeth. Particularly, it has a translucency and color tone equivalent to those of natural teeth. Therefore, it is particularly suitable for a zirconia sintered body to be used for dental applications, and further, suitable for a mill blank such as an artificial tooth material or the like, and an orthodontic bracket.

The entire disclosures of Japanese Patent Application No. 2011-166358 filed on Jul. 29, 2011 and Japanese Patent Application No. 2011-166359 filed on Jul. 29, 2011 including specifications, claims, drawings and summaries are incorporated herein by reference in their entireties.

The invention claimed is:

1. A colored translucent zirconia sintered body, comprising at least one iron compound selected from the group consisting of iron chloride, iron nitrate, iron oxide and iron oxide hydroxide,
yttria in the amount of from 2 to 4 mol %, and
alumina in the amount of 0 wt % to less than 0.25 wt %,
wherein the colored translucent zirconia sintered body has a lightness L* of from 51 to 80 in L*a*b* color system, and has a relative density of at least 99.80%.

2. The colored translucent zirconia sintered body according to claim 1, wherein the lightness L* is from 51 to 70 in L*a*b* color system.

3. The colored translucent zirconia sintered body according to claim 1, wherein the lightness L* is more than 70 and at most 80 in L*a*b* color system.

4. The colored translucent zirconia sintered body according to claim 1, which has a total light transmittance of at least 20% as measured at a sample thickness of 1 mm and with a D65 light source.

5. The colored translucent zirconia sintered body according to claim 1, wherein the content of the iron compound is less than 2,000 ppm as calculated as $Fe_2O_3$.

6. The colored translucent zirconia sintered body according to claim 1, wherein the content of the iron compound is at least 500 ppm as calculated as $Fe_2O_3$.

7. The colored translucent zirconia sintered body according to claim 1, wherein the content of the iron compound is less than 500 ppm as calculated as $Fe_2O_3$.

8. The colored translucent zirconia sintered body according to claim 1, which contains alumina.

9. The colored translucent zirconia sintered body according to claim 1, which has a monoclinic phase transformation depth of at most 10 μm after immersion in a hot water of 140° C. for 24 hours.

10. The colored translucent zirconia sintered body according to claim 9, which has a monoclinic phase transformation depth of at most 10 μm after immersion in a hot water of 140° C. for 72 hours.

11. A dental material obtained by using the colored translucent zirconia sintered body as defined in claim 1.

12. The dental material according to claim 11, which is an orthodontic bracket.

13. The dental material according to claim 11, which is an artificial tooth or an artificial tooth mill blank.

* * * * *